(12) United States Patent
Sun et al.

(10) Patent No.: US 8,921,597 B2
(45) Date of Patent: Dec. 30, 2014

(54) PREPARATION OF BORON CROSSLINKING AGENTS FOR FRACTURING FLUIDS

(75) Inventors: Hong Sun, Houston, TX (US); Qi Qu, Spring, TX (US)

(73) Assignee: Baker Hughes Incorporated, Houston, TX (US)

( * ) Notice: Subject to any disclaimer, the term of this patent is extended or adjusted under 35 U.S.C. 154(b) by 799 days.

(21) Appl. No.: 13/153,805

(22) Filed: Jun. 6, 2011

(65) Prior Publication Data

US 2012/0310011 A1    Dec. 6, 2012

(51) Int. Cl.
C07F 5/02    (2006.01)

(52) U.S. Cl.
CPC ..................................... C07F 5/025 (2013.01)
USPC .......................................................... 564/8

(58) Field of Classification Search
CPC ....................................................... C07F 5/025
USPC ....................................................... 564/8, 9
See application file for complete search history.

(56) References Cited

U.S. PATENT DOCUMENTS

| | | |
|---|---|---|
| 3,284,410 A | 11/1966 | Meinhardt |
| 3,693,720 A | 9/1972 | McDougall et al. |
| 3,974,077 A | 8/1976 | Free |
| 4,328,113 A | 5/1982 | Horodysky et al. |
| 4,474,671 A | 10/1984 | Herd et al. |
| 4,619,776 A | 10/1986 | Mondshine |
| 4,635,727 A | 1/1987 | Anderson et al. |
| 5,145,590 A | 9/1992 | Dawson |
| 5,305,832 A | 4/1994 | Gupta et al. |
| 5,972,850 A | 10/1999 | Nimerick |
| 6,017,855 A | 1/2000 | Dawson et al. |
| 6,060,436 A | 5/2000 | Snyder et al. |
| 7,572,757 B1 | 8/2009 | Gupta et al. |
| 7,687,441 B2 | 3/2010 | Hanes, Jr. et al. |
| 8,173,580 B2 | 5/2012 | De Benedictis et al. |
| 2002/0061288 A1 | 5/2002 | Hubbell et al. |
| 2006/0003900 A1 | 1/2006 | Hanes, Jr. |
| 2006/0089265 A1 | 4/2006 | Hanes, Jr. et al. |
| 2007/0267193 A1 | 11/2007 | Hills et al. |
| 2009/0298719 A1 | 12/2009 | Le et al. |
| 2010/0016182 A1 | 1/2010 | Gupta et al. |
| 2010/0056403 A1 | 3/2010 | Abad et al. |
| 2010/0099913 A1 | 4/2010 | Sun et al. |
| 2010/0197966 A1 | 8/2010 | Sun et al. |

FOREIGN PATENT DOCUMENTS

GB    1545629    5/1979

OTHER PUBLICATIONS

Paushkin, Ya. M.; Panidi, I. S., Tr. Mosk. Inst. Neftekhim. i Gaz. Prom. (1963), 44, 33-8; Russian.*
Paushkin, Ya. M.; Panidi, I. S., Tr. Mosk. Inst. Neftekhim. i Gaz. Prom. (1963), 44, 33-8; CAS abstract.*
Parris et al., "Influence of Pressure on Boron Crosslinked Polymer Gels", Macromolecules, 2008, vol. 41, 8181-8186, published Oct. 11, 2008.
PCT International Search Report and Written Opinion dated May 10, 2010, issued for PCT Application No. PCT/US2009/061174, filed Oct. 19, 2009.
Wiskur, et al., "pKa Values and Geomketries of SEcondary and Tertiary Amines Complexed to Boronic Acids—Implications for Sensor Design", Organic Letters, vol. 3, No. 9, 2001, pp. 1311-1314.
Lei, Cuiyue, et al., Crosslinking of Guar and Guar Derivatives, SPE Annual Technical Conference and Exhibition, Sep. 26-29, 2004, Houston, TX, SPE 90840.
Lei, Cuiyue, et al., Fracturing-Fluid Crosslinking at Low Polymer Concentration, SPE Annual Technical Conference and Exhibition, Oct. 9-12, 2005, Dallas, TX, SPE 96937.

* cited by examiner

*Primary Examiner* — Sudhakar Katakam
*Assistant Examiner* — Kofi Adzamli
(74) *Attorney, Agent, or Firm* — John Wilson Jones; Jones & Smith, LLP

(57) ABSTRACT

Methods for making polyaminoboric acid compounds are provided. The polyaminoboric acid compounds are made by reacting a polyamine with boric acid in the presence of a solvent to produce polyaminoboric acid compounds with more than one boron-nitrogen bond. The polyaminoboric acid compounds are useful as crosslinking agents for fracturing fluids.

13 Claims, No Drawings

PREPARATION OF BORON CROSSLINKING AGENTS FOR FRACTURING FLUIDS

FIELD OF THE INVENTION

The present invention relates to methods for making polyaminoboric acid compounds. These polyaminoboric acid compounds may be used as crosslinking agents for fracturing fluids.

BACKGROUND OF THE INVENTION

Hydraulic fracturing techniques are widely used to enhance oil and gas production from subterranean formations. During hydraulic fracturing, a fluid is injected into a wellbore under high pressure. Once the reservoir partition pressure is exceeded, the fracturing fluid initiates a fracture in the formation that grows during pumping. The treatment design generally requires the fluid to reach a maximum viscosity as it enters the fracture, thereby affecting the fracture length and width. The viscosity of most fracturing fluids is generated from water-soluble polysaccharides, such as galactomannans or cellulose derivatives. Linear gels that can be operated at ambient temperature do not have the necessary viscosity for proper proppant transferring at elevated temperature. The use of crosslinking agents or crosslinkers, such as borate, titanate, or zirconium ions, can further increase the viscosity. The gelled fluid can be accompanied by a proppant that results in its placement within the fracture that has been produced. The proppant remains in the fracture to prevent its closure and to form a conductive channel extending from the wellbore into the formation once the fracturing fluid is recovered.

Guar-based fracturing fluids are the most commonly used fluids in reservoir stimulation. As indicated, stimulation of oil and gas wells has been improved by the ability to crosslink the fracturing fluids to increase their viscosity. Some common crosslinking agents include boron and zirconium or other metallic compounds. Boron crosslinked gels are more commonly used due to their reversibility to mechanical shearing and less harmful environmental properties.

Common boron crosslinkers include boron anhydrides, borate esters, and inorganic borates. Generally for boron crosslinkers, the effective crosslinking species is B—OH, often formed after hydrolysis. For crosslinking, the B—OH moieties must be able to come into proximity with the functional groups on the polymer chains to form a chemical bond and bind the chains together.

U.S. Patent Publication Nos. 2010/0099913 A1 and 2010/0099586 A1, herein incorporated by reference, disclosed a family of poly(aminoborates) that can be used as effective crosslinkers. These applications provided a method to synthesize the poly(aminoborates) through a reaction between polyamines and trialkylborates.

However, this reaction is limited by the boiling point of the trialkylborate, usually trimethylborate. The reaction must be performed in a pressure vessel to increase the temperature and reaction rate to allow the reaction to be driven towards completion but prevent evaporation of the trialkylborate. A closed reaction system makes the reaction more difficult to perform and to monitor, which is a concern for quality control. Furthermore, the commonly used, trimethylborate, is moisture-sensitive and highly flammable with a low flash point. The storage of it requires special conditions, especially for humid climates, which adds to the cost of the final product.

It would be a significant improvement to find a reaction route to synthesize polyboronic crosslinker compounds without the shortcomings associated with using trialkylborate reagents.

SUMMARY OF THE INVENTION

In accordance with the principles of the invention, a method of making polyaminoboric acid compounds comprising reacting boric acid with a polyamine in the presence of a solvent to produce the polyaminoboric acid compounds is presented. This reaction scheme circumvents the drawbacks of using triakylborates as a reactant.

In a simplified aspect of the invention, Reaction 1 portrays boric acid reacting with an amine with the loss of water.

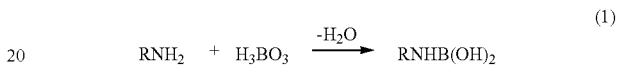
(1)

The R substituent also contains one or more additional amino groups, which would also form boron-nitrogen (B—N) bonds.

In accordance with the principles of the invention, the polyaminoboric acid compounds formed have the structures

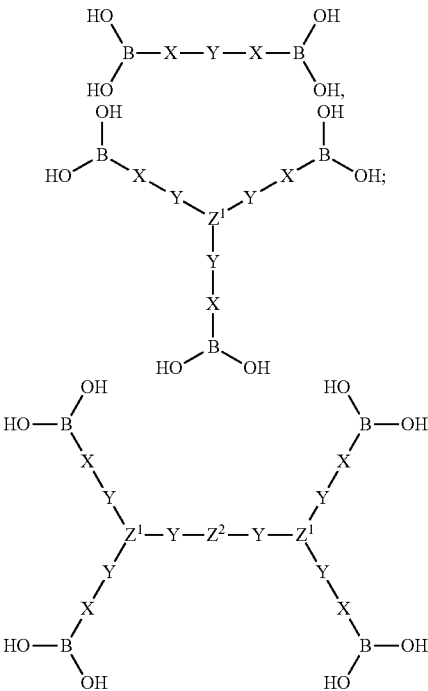

or combinations thereof, wherein X is —NH; Y is a straight chain of (—CH$_2$—), a straight chain with pendant(s), a straight chain with branching, aromatic ring(s) directly connected, aromatic ring(s) indirectly connected, fused aromatic rings, heterocyclic ring(s) directly connected, heterocyclic ring(s) indirectly connected, fused heterocyclic rings, aliphatic ring(s) directly connected, aliphatic ring(s) indirectly connected, fused aliphatic rings, or combinations thereof; and Z$^1$ is —CH, nitrogen, aromatic ring(s), aliphatic ring(s), heterocyclic ring(s) or a trivalent metal or a combination thereof; and Z$^2$ is silicon, oxygen, —NH, alkylene group, alkenyl group, alkynyl group, aromatic ring(s), aliphatic ring(s), heterocyclic ring(s) or a divalent metal atom;

Depending upon the desired structure, many polyamines may be used to make the aminopolyboric acid compounds. In an aspect, the polyamine may comprise ethylenediamine, diethylene triamine (DETA), triethylenetetramine (TETA), tetraethylenepentamine (TEPA), 1,2-propylenediamine, 1,3-propylenediamine, dipropylenetriamine, tripropylenetetramine, tetrapropylenepentamine, ethylene propylene triamine, ethylene dipropylene tetramine, diethylene propylene tetramine, ethylene tripropylene pentamine, diethylene dipropylene pentamine, triethylene propylene pentamine, or combinations thereof.

Many solvents may be used in accordance with the principles of the invention. In an aspect, the solvent may be an alcohol or a glycol. In an aspect, the solvent may be toluene, N,N-dimethylformamide (DMF), or dimethylsulfoxide (DMSO).

The polyaminoboric acid compounds described herein can readily be used as a crosslinking agent for fracturing fluids for subterranean formations. The crosslinked fracturing fluids are provided as embodiments of the present invention. In an aspect, the fracturing fluid comprises a hydratable polymer capable of gelling in the presence of a polyaminoboric acid compound.

In addition to the polyaminoboric acid compounds being used as crosslinking agents, there are other applications for these compounds that fall within the scope of the present invention. These and other features, aspects, and advantages of the present invention will become better understood with reference to the following description and claims.

DETAILED DESCRIPTION OF THE PREFERRED EMBODIMENTS

Illustrative embodiments of the invention are described below as they might be employed in the operation and in the treatment of oilfield applications. In the interest of clarity, not all features of an actual implementation are described in this specification. It will of course be appreciated that in the development of any such actual embodiment, numerous implementation-specific decisions must be made to achieve the developers' specific goals, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments of the invention will become apparent from consideration of the following description.

In accordance with the principles of the present invention, a method to make polyaminoboric acid compounds from boric acid and polyamines is presented. For clarity, a simplified aspect of the invention is presented in Reaction 1. Here, boric acid reacts with a polyamine to produce a polyaminoboric acid compound.

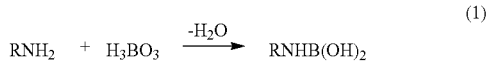

(1)

Here, R represents a substituent that includes one or more additional amino groups, which also form B—N bonds.

While not wanting to be bound by any particular theory, a general reaction mechanism is provided to better elucidate the present invention. Initially, a Lewis acid-base reaction forms an adduct between the boric acid and the amine. The adduct will subsequently undergo a dehydration step, eliminating water, to form the B—N bond. However, it should be recognized that there exists many reaction mechanisms and intermediates that are within the scope of the present invention.

The embodiments of the present invention overcome the shortcomings of using trialkylborates as a reactant. The reaction is not limited by the boiling point of the trialkylborate. The embodiments are more cost effective because boric acid is cheaper and more atom-economical than alkylborates, i.e., it takes less boric acid than trialkylborate to make an equal amount of the crosslinking agent. However, not every advantage is necessary for the embodiments to be in accordance with the present invention.

In a preferred embodiment of the invention, boric acid reacts with a polyamine in the presence of a solvent to produce polyaminoboric acid compounds with the following structures:

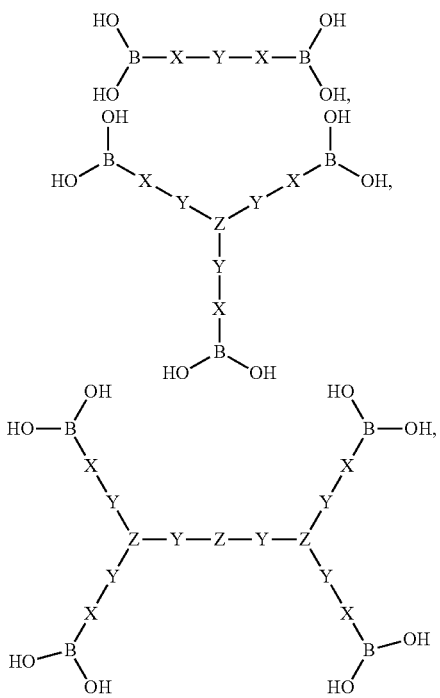

or combinations thereof, wherein X is a —NH to incorporate multiple boron atoms into the structure by the chemical bonding between N and B atoms, Y may be a spacer, which can be straight chain of (—CH$_2$—), straight chain with pendant(s), straight chain with branching, aromatic ring(s) directly connected, aromatic ring(s) indirectly connected, fused aromatic rings, heterocyclic ring(s) directly connected, heterocyclic ring(s) indirectly connected, fused heterocyclic rings, aliphatic ring(s) directly connected, aliphatic ring(s) indirectly connected, fused aliphatic rings, or combinations thereof. For example, Y may be phenylene, biphenylene, triphenylene, fluorene, fluorenone, naphthalene, methylene bisphenylene, stilbene, or combinations thereof. In an aspect, X may also be part of Y when Y has ring structure(s). Z may also be a metal atom, such as, Al, Zr, Ti, Zn, or the like connected to other parts of the structure via chelation and/or other chemical interactions. The general structure of suitable polyboronic compounds can be further extended to dendrimeric "poly"

boronic compounds. Other suitable types of polyboronic compounds will be understood by those of skill in the art and are to be considered within the scope of the present invention.

In an aspect, X is a 2° or 3° amine. In an aspect, Y may be a straight chain of (—CH$_2$—)$_n$ wherein n is an integer from 0 to 6. The straight chain of methylenes may be substituted with an ester, ether, and/or amine group. The straight chain of methylenes may also be substituted with a pendant group comprising an alkyl group, aryl group, ester group, alcohol group, or carboxylic acid group. Y may be an aromatic ring, fused aromatic ring, heterocyclic ring, fused heterocyclic ring, aliphatic ring, fused aliphatic ring, or combinations thereof. For example, Y can be phenylene, biphenylene, triphenylene, fluorene, fluorenone, naphthalene, methylene bisphenylene, stilbene, or combinations thereof. In aspect, Y may comprise 1 to 15 carbons. Y may also contain nitrogen and/or oxygen atoms. In an aspect, polyboronic acid compound may have a molecular weight of less than 1000 g/mol.

In a preferred embodiment of the present invention, the polyaminoboric acid compounds of the present invention have more than one B—N bond in the structure. The number of B—N bonds may be varied depending upon the type of polyamine selected to produce the polyaminoboric acid compounds. In an aspect, the polyaminoboric acid compound may include at least two B—N bonds. In another aspect, the polyaminoboric acid compounds may include as many B—N bonds as there are N atoms in the polyamine. In an aspect, the polyaminoboric acid compounds has more than one B—N bond that provide more than one reaction site to crosslink polymers.

In accordance with the principles of the present invention, the polyaminoboric acid compounds may undergo alkylation at the B—OH moiety to form borate esters. In an aspect, the boric acid may undergo a dehydration reaction with the solvent to form a borate ester. In an aspect, the present invention may produce a mixture of polyaminoboric acid compounds and borate esters.

In accordance with the principles of the invention, boric acid may be reacted with a polyamine containing a 2° amine to produce a polyaminoboric acid compound. For clarity, a simplified aspect of the invention is presented in Reaction 2.

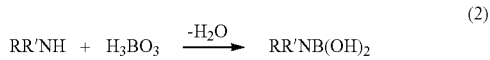

(2)

Here, R and R' represent substituents that may include one or more additional amino groups, which also form B—N bonds.

In an aspect, the polyaminoboric acid compound is:

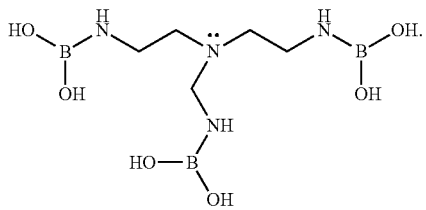 [SMILES: OB(O)NCCN(CCNB(O)O)CNB(O)O]

In aspect, the polyaminoboric acid compound may include the following structures:

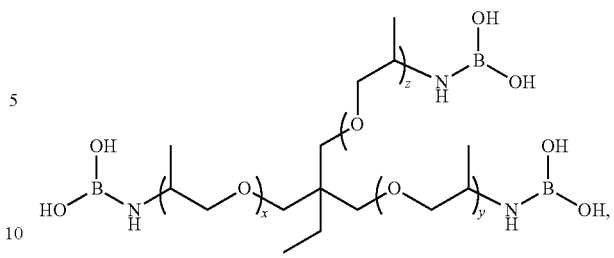

wherein the x, y and z are 1, 2, or 3.

In embodiments of the present invention, various types of polyamines may be used to produce the polyaminoboric acid compounds. In an aspect, the polyamine can include ethylenediamine, diethylene triamine (DETA), triethylenetetramine (TETA), tetraethylenepentamine (TEPA), 1,2-propylenediamine, 1,3-propylenediamine, dipropylenetriamine, tripropylenetetramine, tetrapropylenepentamine, ethylene propylene triamine, ethylene dipropylene tetramine, diethylene propylene pentamine, ethylene tripropylene pentamine, diethylene dipropylene pentamine, triethylene propylene pentamine, polyethylenimine (e.g, Epomin® from Nippon Shokubai, Lupasol™ from BASF, Lupamine™ from BASF, etc.), poly(ethyleneoxy)amines, poly(propyleneoxy)amines (i.e., Jeffamine® T-403 from Huntsman Corporation, Polyetheramine T-5000 from BASF, etc.) or combinations thereof. Other suitable types of polyamines that may be used in the present invention will be apparent to those of skill in the art and are to be considered within the scope of the present invention.

Many solvents may be used in accordance with the principles of the invention. In an aspect, the solvent may comprise methanol, ethanol, propanol, 2-propanol, butanol, 2-butanol, tert-butanol, ethylene glycol, toluene, N,N-dimethylformamide, dimethylsulfoxide, or combinations thereof. In an aspect, the polyamine may be used as both a reactant and solvent. In a preferred embodiment, the invention uses solvents that dissolve the boric acid, the polyamines, and the adduct they form.

In accordance with the principles of the invention, there exists much flexibility in the operation of the reaction. In an aspect, the present invention may begin with wet or dry reagents, which allows for ready procurement of the raw materials. In aspect, the reaction may be performed with excess boric acid or excess polyamine. In a preferred embodiment, the reaction is performed with a stoichiometric ratio of boric acid to the number of amino groups on the polyamine.

In accordance with the principles of the invention, the equilibrium for Reaction 1 may be shifted to the product side in many ways. In an aspect, excess reactants may be used. In an aspect, the reaction mixture may be heated. In another aspect, water may be removed to shift the reaction equilibrium towards completion. In an embodiment, the water may be azeotropically removed from the reaction mixture with any solvent that forms an azeotrope with water, such as toluene, 1-butanol, or benzene. In another embodiment, water may be removed by molecular sieves or dry agents, such as calcium chloride, calcium sulfate, sodium sulfate, or magnesium sulfate.

In a preferred embodiment of the present invention, a crosslinked fracturing fluid composition is provided. In this embodiment, the fracturing fluid includes a hydratable polymer capable of gelling in the presence of a crosslinking agent comprising an polyaminoboric acid compound. Various types of polyaminoboric acid compounds can be used in embodiments of the present invention, as described herein. Typical hydratable polymers include, but are not limited to, polysaccharides, guar gum, guar gum derivatives, locust bean gum, karaya gum, carboxymethyl cellulose, carboxymethylhydroxyethyl cellulose, hydroxyethyl cellulose, or combinations thereof. The methods and compositions described herein may be used with various types of fracturing fluid systems. The hydratable polymer may be varied depending upon the needs of a particular fracturing job. Other suitable hydratable polymers that are compatible with the methods and compositions described herein may be used and are to be considered within the scope of the present invention.

The concentrations of the components within the fracturing fluid may be varied in the various embodiments of the present invention. For example, the polyaminoboric acid compound may be present in a range of about 0.02 vol. % to about 0.5 vol. % of the fracturing fluid composition; alternatively, in a range of about 0.10 vol. % to about 0.25 vol. %. In an aspect, the polyaminoboric acid compounds may be present in a range that is effective for achieving the desired viscosity of the resulting fracturing fluid, as will be apparent to those of skill in the art.

Besides the polymer and crosslinking agents described herein, various additives may be used in the embodiments of the present invention. Additives used in the oil and gas industry and known in the art, including but not limited to, corrosion inhibitors, non-emulsifiers, iron control agents, delay additives, silt suspenders, flowback additives, pH adjusting agents, clay stabilizer, surfactants, and gel breakers, may also be used in embodiments of the present invention. Proppants including, but not limited to, frac sand, resin coated sand, quartz sand grains, ceramic proppant, tempered glass beads, rounded walnut shell fragments, aluminum pellets, and nylon pellets at desired size may also be used. Typically, the proppant is used in concentrations that range between about 1 pound per gallon of the fracturing fluid composition to about 8 pounds per gallon of the fracturing fluid composition. Other suitable additives useful in the present invention will be apparent to those of skill in the art and are to be considered within the scope of the present invention.

EXAMPLES

The following examples are included to demonstrate the use of compositions in accordance with the embodiments of the present invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the scope of the invention.

Example 1

This example shows how polyaminoboric acid compounds are generally synthesized. The synthetic scheme may be extended to other type of polyaminoboric acid compounds. A 500 mL, 3-necked, round-bottom flask was equipped with a Dean-Stark trap with a reflux condenser and a temperature indicator. Into the flask was added 100 mL of toluene, 18.6 g of boric acid and a magnetic stir bar. 14.6 g of water-free tris(2-aminoethyl)amine was added dropwise to the reaction mixture. A slight exotherm was observed. Slowly, the insoluble boric acid turned into a sticky, yellow solid which could not be agitated effectively. The reaction mixture was heated under reflux. An opaque vapor condensed and collected in the Dean-Stark trap at 90° C. The mixture separated into a top toluene layer and a bottom water layer. After 1 hour, 5.4 g of water was collected in the Dean-Stark trap. After cooling the reaction mixture, the sticky solid turned into yellow, brittle crystals. The toluene layer was decanted and the solid was air dried. Infrared spectroscopy (IR) was performed on the solid. The loss of water and the IR spectrum confirmed the reaction between boric acid and tris(2-aminoethyl)amine.

Example 2

This example demonstrates how polyaminoboric acid compounds may be synthesized in a homogeneous reaction medium. 31 g of boric acid and 100 g of ethylene glycol were added to a 500 mL, 3-necked, round-bottom flask equipped with a Dean-Stark trap with a reflux condenser, a stir bar, and a temperature indicator. The reaction mixture was stirred and heated to form a clear solution. When the reaction mixture reached a temperature of 57° C., 40 mL of butanol was added. The solution was heated under reflux. 22.7 g of water was collected in the Dean-Stark trap. The mixture was cooled and 19 g of tetraethylene pentamine was added dropwise. The reaction mixture was re-heated to remove any residual water and butanol. The reaction mixture was allowed to cool to room temperature. Upon cooling, the reaction mixture turned slightly viscous with a light yellow color. IR spectroscopy was performed on the product. The IR spectrum confirmed the reaction between boric acid and tetraethylene pentamine.

Example 3

This example demonstrates how polyaminoboric acid compounds can be used to crosslink guar solutions. A 20 ppt of guar (GW-3, commercially available from Baker Hughes Inc.) solution was combined and crosslinked with 2 gpt (gallons per 1000 gallons) (2 L/m$^3$) of the polyaminoboric acid product from Example 2. The resulting crosslinked gel was tested on a Fann 50 instrument at 93.3° C. The rheology data are summarized in Table 1.

TABLE 1

Rheology of 20 ppt of GW-3 Crosslinked with 2 gpt of Poly(aminoborate)

| Time (min) | n' | Viscosity (cP) | | |
|---|---|---|---|---|
| | | 40 s$^{-1}$ | 100 s$^{-1}$ | 170 s$^{-1}$ |
| 2.1 | 0.5173 | 1116 | 717 | 555 |
| 32.1 | 0.4231 | 625 | 369 | 271 |
| 62.1 | 0.5315 | 647 | 421 | 329 |
| 92.1 | 0.3829 | 684 | 389 | 280 |
| 122.1 | 0.4931 | 669 | 421 | 321 |
| 152.1 | 0.5904 | 605 | 416 | 335 |
| 182.1 | 0.4134 | 646 | 377 | 276 |

While the compositions and methods in accordance with the present invention have been described in terms of preferred embodiments, it will be apparent to those of skill in the art that variations can be applied to the compositions and/or methods and in the steps or in the sequence of steps described herein without departing from the concept, spirit and scope of the invention. Moreover, it will be apparent that certain agents that are chemically related can be substituted for the agents described herein while the same or similar results would be achieved. All such similar substitutes and modifications apparent to those skilled in the art are deemed to be within the scope and concept of the invention. It is intended that the specification be considered exemplary only, with the scope and spirit of the invention being indicated by the claims which follow.

What is claimed is:

1. A method of making a polyaminoboric acid compound comprising contacting boric acid with a polyamine in the presence of a solvent, wherein the polyaminoboric acid compound is:

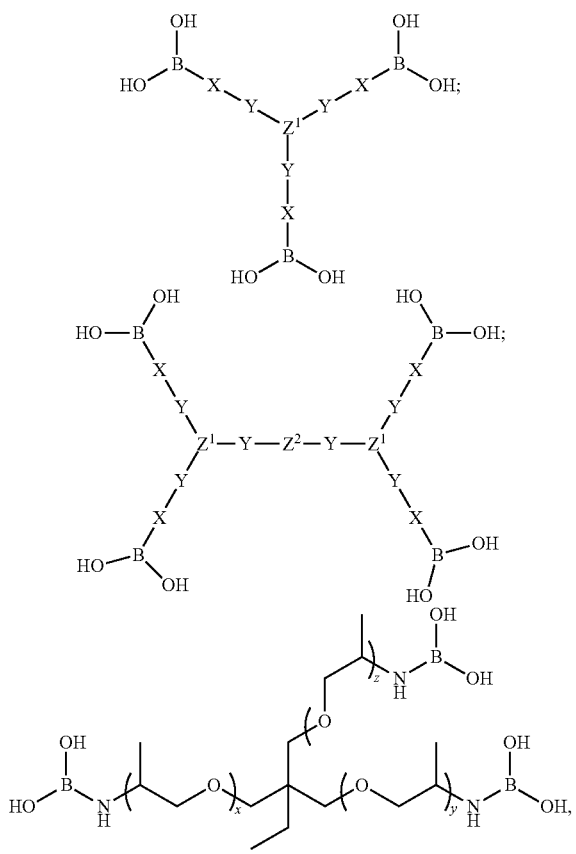

or combinations thereof
wherein
X is —NH;
Y is a straight chain of (—CH$_2$—), a straight chain with pendant(s), a straight chain with branching, aromatic ring(s) directly connected, aromatic ring(s) indirectly connected, fused aromatic rings, heterocyclic ring(s) directly connected, heterocyclic ring(s) indirectly connected, fused heterocyclic rings, aliphatic ring(s) directly connected, aliphatic ring(s) indirectly connected, fused aliphatic rings, or combinations thereof;
$Z^1$ is —CH, nitrogen, aromatic ring(s), aliphatic ring(s), heterocyclic ring(s) or a combination thereof; and $Z^2$ is silicon, oxygen, —NH, alkylene group, alkenyl group, alkynyl group, aromatic ring(s), aliphatic ring(s) or heterocyclic ring(s); and
x, y and z are 1, 2 or 3.

2. The method of claim 1, wherein the polyaminoboric acid compound comprises:

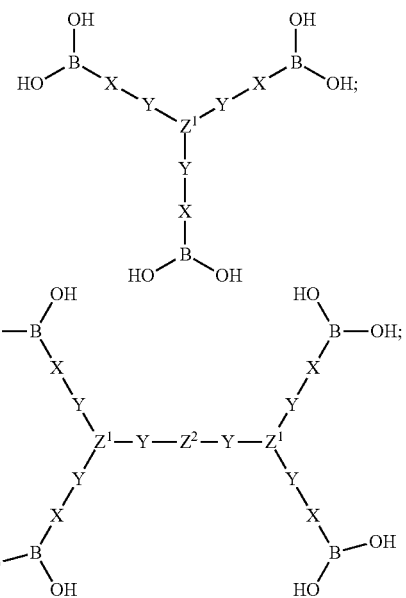

or combinations thereof.

3. The method of claim 1, wherein the polyamine comprises diethylene triamine (DETA), triethylenetetramine (TETA), tetraethylenepentamine (TEPA), 1,2-propylenediamine, 1,3-propylenediamine, dipropylenetriamine, tripropylenetetramine, tetrapropylenepentamine, ethylene propylene triamine, ethylene dipropylene tetramine, diethylene propylene tetramine, ethylene tripropylene pentamine, diethylene dipropylene pentamine, triethylene propylene pentamine, tris(2-aminoethyl)amine, or combinations thereof.

4. The method of claim 1, wherein the solvent comprises methanol, ethanol, propanol, 2-propanol, butanol, 2-butanol, tert-butanol, ethylene glycol, toluene, N,N-dimethylformamide, dimethylsulfoxide, or combinations thereof.

5. A method of making a polyaminoboric acid compound comprising contacting a polyamine with boric acid in the presence of a solvent to produce the polyaminoboric compound, wherein the polyamine comprises diethylene triamine (DETA), triethylenetetramine (TETA), tetraethylenepentamine (TEPA), 1,2-propylenediamine, 1,3-propylenediamine, dipropylenetriamine, tripropylenetetramine, tetrapropylenepentamine, ethylene propylene triamine, ethylene dipropylene tetramine, diethylene propylene tetramine, ethylene tripropylene pentamine, diethylene dipropylene pentamine, triethylene propylene pentamine, tris(2-aminoethyl)amine, or combinations thereof.

6. The method of claim 5, wherein the polyaminoboric acid compound comprises:

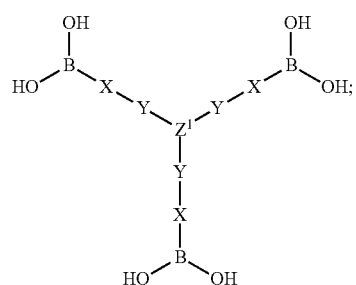

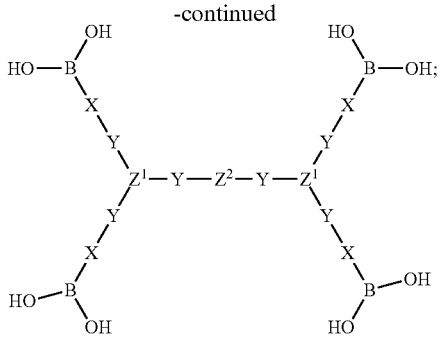

or combinations thereof,

X is —NH;

Y is a straight chain of (—CH$_2$—), a straight chain with pendant(s), a straight chain with branching, aromatic ring(s) directly connected, aromatic ring(s) indirectly connected, fused aromatic rings, heterocyclic ring(s) directly connected, heterocyclic ring(s) indirectly connected, fused heterocyclic rings, aliphatic ring(s) directly connected, aliphatic ring(s) indirectly connected, fused aliphatic rings, or combinations thereof;

$Z^1$ is —CH, nitrogen, aromatic ring(s), aliphatic ring(s), heterocyclic ring(s) or a combination thereof; and $Z^2$ is silicon, oxygen, —NH, alkylene group, alkenyl group, alkynyl group, aromatic ring(s), aliphatic ring(s) or heterocyclic ring(s).

7. The method of claim 5, wherein the solvent comprises methanol, ethanol, propanol, 2-propanol, butanol, 2-butanol, tert-butanol, ethylene glycol, toluene, N,N-dimethylformamide, dimethylsulfoxide, or combinations thereof.

8. A method of making a polyaminoboric acid compound comprising:
   a. reacting a mixture of boric acid, a polyamine, and a solvent, wherein the polyamine comprises diethylene triamine (DETA), triethylenetetramine (TETA), tetraethylenepentamine (TEPA), 1,2-propylenediamine, 1,3-propylenediamine, dipropylenetriamine, tripropylenetetramine, tetrapropylenepentamine, ethylene propylene triamine, ethylene dipropylene tetramine, diethylene propylene tetramine, ethylene tripropylene pentamine, diethylene dipropylene pentamine, triethylene propylene pentamine, tris(2-aminoethyl)amine, or a combination thereof and;
   b. removing water from the mixture to form the polyaminoboric acid compound.

9. The method of claim 8, wherein the solvent comprises methanol, ethanol, propanol, 2-propanol, butanol, 2-butanol, tert-butanol, ethylene glycol, toluene, N,N-dimethylformamide, dimethylsulfoxide, or combinations thereof.

10. The method of claim 8, wherein the polyaminoboric compound comprises at least two B—N bonds.

11. The method of claim 8, wherein the polyaminoboric compound comprises an equivalent number of B—N bonds as N atoms in the polyamine.

12. The method of claim 8, wherein the polyamine is tris(2-aminoethyl)amine.

13. The method of claim 8, wherein the polyamine is tetraethylene pentamine.

* * * * *